United States Patent
Refetoff et al.

(10) Patent No.: US 12,390,432 B2
(45) Date of Patent: Aug. 19, 2025

(54) METHODS FOR TREATING ALLAN-HERNDON-DUDLEY SYNDROME

(71) Applicants: PriZm, LLC, Chandler, AZ (US); The University of Miami, Coral Gables, FL (US); The University of Chicago, Chicago, IL (US)

(72) Inventors: Samuel Refetoff, Chicago, IL (US); Roy Weiss, Miami Beach, FL (US); Khemraj Hirani, Chandler, AZ (US)

(73) Assignees: PriZm, LLC, Chandler, AZ (US); The University of Miami, Coral Gables, FL (US); The University of Chicago, Chicago, IL (US)

( * ) Notice: Subject to any disclaimer, the term of this patent is extended or adjusted under 35 U.S.C. 154(b) by 0 days.

(21) Appl. No.: 18/350,116

(22) Filed: Jul. 11, 2023

(65) Prior Publication Data
US 2024/0009158 A1    Jan. 11, 2024

Related U.S. Application Data

(60) Provisional application No. 63/388,242, filed on Jul. 11, 2022.

(51) Int. Cl.
*A61K 31/192* (2006.01)
*A61P 5/16* (2006.01)

(52) U.S. Cl.
CPC .............. *A61K 31/192* (2013.01); *A61P 5/16* (2018.01)

(58) Field of Classification Search
CPC .................................. A61K 31/192; A61P 5/16
See application file for complete search history.

(56) References Cited

U.S. PATENT DOCUMENTS

| | | | |
|---|---|---|---|
| 6,534,676 | B2 | 3/2003 | Morkin |
| 8,802,240 | B2 | 8/2014 | Davis |
| 2002/0151594 | A1 | 10/2002 | Morkin |
| 2007/0286856 | A1 | 12/2007 | Brown |
| 2017/0342380 | A1 | 11/2017 | Petratos |
| 2022/0362191 | A1 | 11/2022 | Tengler |
| 2023/0285342 | A1 | 9/2023 | Tengler |

FOREIGN PATENT DOCUMENTS

| | | | | |
|---|---|---|---|---|
| WO | 2008106213 | | 9/2008 | |
| WO | WO2012/171065 | * | 12/2012 | ................. A61P 5/14 |
| WO | WO-2012171065 A1 | * | 12/2012 | ............ A61K 31/192 |
| WO | 2021216896 | | 10/2021 | |

OTHER PUBLICATIONS

James M. Kidd, Tomefa E. Asempa, Kamilia Abdelraouf, Chapter 13 Therapeutic drug monitoring, Editor(s): Adeboye Adejare, Remington (Twenty-third Edition), pp. 243-262, (Year: 2021).*
Egorin, Merrill J. "Therapeutic drug monitoring and dose optimisation in oncology." In New approaches in cancer pharmacology: drug design and development, pp. 75-91. Berlin, Heidelberg: Springer Berlin Heidelberg, 1992 (Year: 1992).*
Ladenson, Paul W., M. McCarren, E. Morkin, R. G. Edson, Mei-Chiung Shih, S. R. Warren, J. G. Barnhill et al. The Journal of Clinical Endocrinology & Metabolism 95, No. 3 (2010): 1349-1354) (Year: 2010).*
Iwayama et al., "Adeno Associated Virus 9-Based Gene Therapy Delivers a Functional Monocarboxylate Transporter 8", Improving Thyroid Hormone Availability to the Brain of Mct8-Deficient Mice, Thyroid, (Sep. 1, 2016), vol. 26, doi: 10.1089/thy.2016.0060, pp. 1311-1319, XP093042508.
Verge et al., "Dilodothyropropionic Acid (DITPA) in the Treatment of MCT8 Deficiency", The Journal of Clinical Endocrinology & Metabolism, (Sep. 19, 2012), vol. 97, No. 12, doi: 10.1210/jc.2012-2556, pp. 4515-4523, XP055475999.
Alfonso Massimiliano Ferrara, Liao Xiao-Hui, Gil-Ibáñez Pilar, Bernal Juan, Weiss Roy E., Dumitrescu Alexandra M., Refetoff Samuel, "Placenta Passage of the Thyroid Hormone Analog DITPA to Male Wild-Type and Mct8-Deficient Mice", Endocrinology, The Endocrine Society, US, US , (Oct. 1, 2014), vol. 155, No. 10, doi: 10.1210/en.2014-1085, ISSN 0013-7227, pp. 4088-4093, XP055475997.
Allan W, Herndon CN, Dudley FC. Some examples of the inheritance of mental deficiency: apparently sex-linked idiocy and microcephaly. Am J Ment Defic. 1944;48:325-334.
Dumitrescu AM, Liao XH, Best TB, Brockmann K, Refetoff S. A Novel Syndrome Combining Thyroid and Neurological Abnormalities Is Associated with Mutations in a Monocarboxylate Transporter Gene. Am J Hum Genet. 2004,74 (1):168-175.
Di Cosmo C, Liao XH, Dumitrescu AM, Weiss RE, Refetoff S. A thyroid hormone analogue with reduced dependence on the monocarboxylate transporter 8 (MCT8) for tissue transport. Endocrinology. 2009;150(9):4450-4458.
Liao X-H, P. A, Shelest O, et al. AAV9-MCT8 delivery at juvenile stage ameliorates neurological and behavioral deficits in an Allan-Herndon-Dudley Syndrome mouse model. 2021.
Grijota-Martinez C, Bárez-López S, Gómez-Andrés D, Guadaño-Ferraz A. MCT8 Deficiency: The Road to Therapies for a Rare Disease. Frontiers in Neuroscience. 2020; 14.
Iwayama H, Liao XH, Braun L, Barez-Lopez S, Kaspar B, Weiss RE, Dumitrescu AM, Guadano-Ferraz A, Refetoff S. Adeno Associated Virus 9-Based Gene Therapy Delivers a Functional Monocarboxylate Transporter 8, Improving Thyroid Hormone Availability to the Brain of Mct8-Deficient Mice. Thyroid. 2016;26(9):1311-1319.

(Continued)

*Primary Examiner* — James H Alstrum-Acevedo
*Assistant Examiner* — Carolyn L. Ladd
(74) *Attorney, Agent, or Firm* — FULLER IP LAW LLC; Scott H. Blackman

(57) ABSTRACT

The present subject matter is directed to methods of treating Allan-Herndon-Dudley syndrome comprising administering 3,5-diiodothyropropionic acid (DITPA) to a subject in need thereof, wherein the DITPA administration reduces triiodothyronine ("T3") serum levels to normal, increases T3 brain levels to normal, and maintains normal serum levels of thyroxine (T4) and thyroid stimulating hormone (TSH). The subject may be a child or an adult.

15 Claims, No Drawings

(56) References Cited

OTHER PUBLICATIONS

Romitti M, de Faria da Fonsecaa B, G. D. P. G. A. T, E. ES, Van Simaeys G, Chomette L, Lasolle H, Monestier O, Figini Kasprzyk D, Detours V, Pal Singh S, Goldman G, Refetoff S, Costagliola S. Transplantable human thyroid organoids generated from embryonic stem cells to rescue hypothyroidism. 2021. https://doi.org/10.1101/2021.12.01.470729.

Verge CF, Konrad D, Cohen M, Di Cosmo C, Dumitrescu AM, Marcinkowski T, Hameed S, Hamilton J, Weiss RE, Refetoff S. Diiodothyropropionic Acid (DITPA) in the Treatment of MCT8 Deficiency. J Clin Endocrinol Metab. 2012;97 (12):4515-4523.

Cicatiello AG, Di Girolamo D, Dentice M. Metabolic Effects of the Intracellular Regulation of Thyroid Hormone: Old Players, New Concepts. Front Endocrinol (Lausanne). 2018;9:474-474.

Ferrara AM, Liao XH, Gil-Ibanez P, Marcinkowski T, Bernal J, Weiss RE, Dumitrescu AM, Refetoff S. Changes in Thyroid Status During Perinatal Development of MCT8-Deficient Male Mice. Endocrinology. 2013; 154(7):2533-2541.

Martinez ME, Hernandez A. The Type 3 Deiodinase Is a Critical Modulator of Thyroid Hormone Sensitivity in the Fetal Brain. Frontiers in Neuroscience. 2021; 15.

Hogan MC, Griffin MD, Rossetti S, Torres VE, Ward CJ, Harris PC. PKHDL1, a homolog of the autosomal recessive polycystic kidney disease gene, encodes a receptor with inducible T lymphocyte expression. Hum Mol Genet. 2003; 12 (6):685-698.

Kurdyukov S, Bullock M. DNA Methylation Analysis: Choosing the Right Method. Biology (Basel). 2016;5(1):3.

Mancino G, Sibilio A, Luongo C, Di Cicco E, Miro C, Cicatiello AG, Nappi A, Sagliocchi S, Ambrosio R, De Stefano MA, Di Girolamo D, Porcelli T, Murolo M, Saracino F, Perruolo G, Formisano P, Stornaluolo M, Dentice M. The Thyroid Hormone Inactivator Enzyme, Type 3 Deiodinase, Is Essential for Coordination of Keratinocyte Growth and Differentiation. Thyroid. 2020;30(7):1066-1078.

Hernandez A, Martinez E, Fiering S, Parlow A, Galton V, St. Germain D. The type 3 deiodinase (D3)-deficient mouse provides a new model of developmental central hypothyroidism. Paper presented at: 76th Annual Meeting of the American Thyroid Association2004; Vancouver, BC, Canada.

Ng L, Lyubarsky A, Nikonov SS, Ma M, Srinivas M, Kefas B, St Germain DL, Hernandez A, Pugh EN, Jr., Forrest D. Type 3 deiodinase, a thyroid-hormone-inactivating enzyme, controls survival and maturation of cone photoreceptors. J Neurosci. 2010;30(9):3347-3357.

Williams AJ, Robson H, Kester MHA, van Leeuwen JPTM, Shalet SM, Visser TJ, Williams GR. Iodothyronine deiodinase enzyme activities in bone. Bone. 2008;43(1):126-134.

Wu X, Ivanchenko MV, Al Jandal H, Cicconet M, Indzhykullan AA, Corey DP. PKHD1L1 is a coat protein of hair-cell stereocilia and is required for normal hearing. Nat Commun. 2019; 10(1):3801.

van Geest, F.S. et al. "Long-term efficacy of T3 analogue Triac in children and adults with MCT8 deficiency: a real-life retrospective cohort study." The Journal of Clinical Endocrinology & Metabolism 107, No. 3 (2022) : e1136-e1147.

\* cited by examiner

METHODS FOR TREATING ALLAN-HERNDON-DUDLEY SYNDROME

CROSS-REFERENCE TO RELATED APPLICATION

This application claims the benefit of U.S. Provisional Patent Application No. 63/388,242, filed on Jul. 11, 2022, the content of which is incorporated herein by reference in its entirety.

TECHNICAL FIELD

The present technology is directed to methods of treating Allan-Herndon-Dudley syndrome comprising administering 3,5-diiodothyropropionic acid (DITPA) to a subject in need thereof, wherein administration of about 2.5 milligrams per kilogram of body weight of the subject per day reduces triiodothyronine ("T3") serum levels to normal, increases T3 brain levels to normal and maintains normal serum levels of thyroxine (T4) and thyroid stimulating hormone (TSH).

BACKGROUND ART

Allan-Herndon-Dudley Syndrome ("ARDS") is an X-linked recessive developmental disorder causing intellectual disability and movement issues in males. Specifically, patients with ARDS have a mutant SLC16A2 gene resulting in a malformed monocarboxylate transporter 8 ("MCT8") protein. Symptoms of ARDS are caused by a lack of cellular uptake of the thyroid hormone triiodothyronine ("T3"), which is normally transported across the cell membrane by MCT8. This MCT8 deficiency leads to a lack of T3 in tissues that need T3 to function properly contributing to an accumulation of T3 in the blood serum. The other thyroid hormone thyroxine ("T4") usually remains at normal serum levels in ARDS patients but may also be slightly reduced from a normal level. Thyroid stimulating hormone ("TSH") is normal to slightly elevated in ARDS patients.

Currently, no treatment for ARDS has been approved by the United States Food and Drug Administration. Clinical trials have been completed for the drug, triiodothyroacetic acid ("TRIAC"), for use in the treatment of ARDS. However, TRIAC shares a close structural similarity to T3, which makes it difficult to accurately assess T3 serum levels. Further, TRIAC has been shown to significantly reduce thyroxine ("T4") serum levels. See, Groeneweg et al. *Lancet Diabetes Endocrinol.* 2019 September; 7(9); 695-706.

3,5-diiodothyropropionic acid ("DITPA") is another thyroid hormone analog that has been studied for treatment of ARDS. However, as mentioned above, DITPA has not been approved for use in the treatment of AHDS. This lack of approval may be due to a lack of effective dosing regimens, stable and effective compositions and extensive pharmacological assessments. While WO/2012/171065, published Dec. 20, 2012, attempts to establish DITPA dosing regimens for ARDS patients, this publication offers only theoretical examples.

Thus, there is a need in the art for specific DITPA dosages that are effective at treating ARDS and symptoms of ARDS by decreasing T3 levels while maintaining normal T4 and TSH levels.

DISCLOSURE

The Applicant has discovered dosages of 3,5-diiodothyropropionic acid ("DITPA") that are surprisingly effective for the treatment of Allan-Herndon-Dudley Syndrome ("AHDS") while maintaining normal serum levels of thyroxine ("T4") and thyroid stimulating hormone ("TSH").

The present technology is directed to methods of treating Allan-Herndon-Dudley syndrome comprising administering 3,5-diiodothyropropionic acid (DITPA) to a subject in need thereof, wherein administration of about 2.5 milligrams per kilogram of body weight of the subject per day reduces triiodothyronine ("T3") serum levels to normal, increases T3 brain levels to normal, increases or maintains normal serum levels of thyroxine (T4) and decreases or maintains normal thyroid stimulating hormone (TSH) serum levels.

DESCRIPTION OF EMBODIMENTS

The Applicant has discovered dosages of 3,5-diiodothyropropionic acid ("DITPA") that are surprisingly effective for the treatment of Allan-Herndon-Dudley Syndrome ("AHDS") while maintaining normal serum levels of thyroxine ("T4") and thyroid stimulating hormone ("TSH").

Maintaining normal serum levels of T4 and TSH is important as T4 is the main thyroid hormone that crosses the blood brain barrier and TSH regulates the production of both T3 and T4 by the thyroid.

In one embodiment, the present subject matter is directed to methods of treating Allan-Herndon-Dudley syndrome comprising the following steps:
 a) administering 3,5-diiodothyropropionic acid ("DITPA") at a first daily dosage for two weeks to a subject in need thereof;
 b) administering DITPA at a second daily dosage for two weeks to the subject wherein the second daily dosage is greater than the first daily dosage;
 c) measuring triiodothyronine ("T3") serum levels in the subject; and
 d) adjusting dosage of DITPA administered to the subject based on T3 serum levels of the subject wherein if the T3 serum levels are too high a third daily dosage is administered wherein the third daily dosage in greater than the second daily dosage and wherein if the T3 serum levels are too low a fourth daily dosage is administered wherein the fourth daily dosage is less than the second daily dosage.

In another embodiment, the present subject matter is directed to methods of treating Allan-Herndon-Dudley syndrome comprising the following steps:
 a) administering 3,5-diiodothyropropionic acid ("DITPA") at a first daily dosage for two weeks to a subject in need thereof; and
 b) administering DITPA at a second daily dosage for two weeks to the subject wherein the second daily dosage is greater than the first daily dosage, wherein administration begins three days following birth of the subject.

In one embodiment, the present technology is directed to methods of treating ARDS comprising administering DITPA to a subject in need thereof, wherein administration of about 2.5 milligrams per kilogram of body weight of the subject per day reduces T3 serum levels to normal, increases T3 brain levels to normal, increases or maintains normal serum levels of thyroxine (T4), and decreases or maintains normal thyroid stimulating hormone (TSH) serum levels.

As used herein the term "normal T3 serum levels" refers to a T3 serum level that is considered normal for the age of the subject.

As used herein the term "normal T3 brain levels" refers to a T3 brain level that is considered normal for the age of the subject.

As used herein the term "normal T4 serum levels" refers to a T4 serum level that is considered normal for the age of the subject.

As used herein the term "normal TSH serum levels" refers to a TSH serum level that is considered normal for the age of the subject.

As used herein "normal" T3, T4 and TSH serum levels by age of the subject is based on levels disclosed in Lem et al., Serum thyroid hormone levels in healthy children from birth to adulthood and in short children born small for gestational age, *J Clin Endocrinol Metab,* 2012 September, 97(9), 3170-8, doi: 10.1210/jc.2012-1759, Epub 2012 Jun. 26.

As used herein the term "too high" with regard to T3 serum level refers to a T3 serum level that is more than about 15% over T3 serum levels considered normal for the age of the subject.

As used herein the term "too low" with regard to T3 serum level refers to a T3 serum level that is more than about 15% under T3 serum levels considered normal for the age of the subject.

In a preferred embodiment, the daily dosage of DITPA is administered to a subject in need thereof once a day, more preferably the daily dosage of DITPA is divided in two parts and each part is administered every 12 hours or twice daily, and most preferably the daily dosage of DITPA is divided into three parts and each part is administered every 8 hours or three times a day. The subject may be a child or an adult.

In another preferred embodiment, the method of treating ARDS comprises the following steps:
a) administering DITPA daily at a first daily dosage for two weeks to a subject in need thereof; and
b) administering DITPA daily at a second daily dosage for two weeks to the subject wherein the second daily dosage is greater than the first daily dosage.

Preferably, the daily administration begins three or more days following birth of the subject.

In a preferred embodiment, the method of treating Allan-Herndon-Dudley syndrome comprises the following steps:
a) administering DITPA daily at a first daily dosage for two weeks to a subject in need thereof;
b) administering DITPA daily at a second dosage for two weeks to the subject wherein the second daily dosage is greater than the first daily dosage;
c) measuring triiodothyronine ("T3") serum levels in the subject, wherein if T3 serum levels are normal the second daily dosage is administered daily;
d) optionally, adjusting daily dosage of DITPA administered to the subject based on T3 serum levels of the subject measured in step c) wherein if the T3 serum levels are too high a third dosage is administered daily wherein the third daily dosage in greater than the second daily dosage and wherein if the T3 serum levels are too low a fourth dosage is administered daily wherein the fourth daily dosage is less than the second daily dosage; and
e) optionally, measuring T3 serum levels of the subject about 28 days following initial administration of the third or fourth dosage wherein if T3 serum levels are normal the third or fourth dosage is administered daily; and
f) optionally, adjusting daily dosage of DITPA administered to the subject based on T3 serum levels of the subject measured in step e) wherein if the T3 serum levels are too low following daily administration of the third dosage then the subject is administered the second daily dosage and wherein if the T3 serum levels are too low following daily administration of the fourth dosage then the subject is administered the first dosage daily and wherein if the T3 serum levels are too high following daily administration of the fourth dosage then the subject is administered the second dosage daily.

In a preferred embodiment, the first dosage is about 1 milligram per kilogram of body weight of the subject per day ("mg/kg/day").

In another preferred embodiment, the second dosage is about 2 mg/kg/day.

In another preferred embodiment, the third dosage is about 2.5 mg/kg/day.

In another preferred embodiment, the fourth dosage is about 1.5 mg/kg/day.

In a preferred embodiment, DITPA is administered to a subject who is less than 18 years old.

In a preferred embodiment, administration of DITPA occurs via the oral route.

In one embodiment, DITPA may be formulated in a composition comprising DITPA, or a salt thereof, and one or more pharmaceutically acceptable excipients.

In a preferred embodiment, DITPA, or a salt thereof, may present in the pharmaceutical compositions of the present subject matter at a concentration from about 0.001% to about 10% w/w or w/v. The formulation may be administered, for example, orally. Oral tablets may be, for example, dispersible tablets for oral suspension. Oral dosing may range, for example, from 0.5 to 2.5 mg/kg/day based on T3 levels of the patient.

In a preferred embodiment, the one or more pharmaceutically acceptable excipients may be present in the pharmaceutical compositions of the present subject matter at a concentration from about 90% to about 99.999% w/w or w/v.

Pharmaceutically acceptable excipients suitable for use in the present technology include, but are not limited to, disintegrants, binders, fillers, plasticizers, lubricants, permeation enhancers, surfactants, sweeteners, sweetness enhancers, flavoring agents and pH adjusting agents.

The term "disintegrants" as used herein refers to pharmaceutically acceptable excipients that facilitate the disintegration of the tablet once the tablet contacts water or other liquids. Disintegrants suitable for use in the present technology include, but are not limited to, natural starches, such as maize starch, potato starch etc., directly compressible starches such as starch 1500, modified starches such as carboxymethyl starches, sodium hydroxymethyl starches and sodium starch glycolate and starch derivatives such as amylose, cross-linked polyvinylpyrrolidones such as crospovidones, modified celluloses such as cross-linked sodium carboxymethyl celluloses, sodium hydroxymethyl cellulose, calcium hydroxymethyl cellulose, croscarmellose sodium, low-substituted hydroxypropyl cellulose, alginic acid, sodium alginate, microcrystalline cellulose, methacrylic acid-divinylbenzene copolymer salts and combinations thereof.

Binders suitable for use in the present subject matter include, but are not limited to, polyethylene glycols, soluble hydroxyalkyl celluloses, polyvinylpyrrolidone, gelatins, natural gums and combinations thereof.

Fillers suitable for use in the present application include, but are not limited to, dibasic calcium phosphate, calcium phosphate tribasic, calcium hydrogen phosphate anhydrous, calcium sulfate and dicalcium sulfate, lactose, sucrose, amylose, dextrose, mannitol, inositol, and combinations thereof.

Plasticizers suitable for use in the present subject matter include, but are not limited to, microcrystalline cellulose, triethyl citrate, poly-hexanediol, acetylated monoglyceride, glyceryl triacetate, castor oil, and combinations thereof.

Lubricants suitable for use in the present technology include, but are not limited to, magnesium stearate, sodium stearyl fumarate, stearic acid, glyceryl behenate, micronized polyoxyethylene glycol, talc, silica colloidal anhydrous and combinations thereof.

Permeation enhancers suitable for use in the present technology include, but are not limited to, precipitated silicas, maltodextrins, β-cyclodextrins menthol, limonene, carvone, methyl chitosan, polysorbates, sodium lauryl sulfate, glyceryl oleate, caproic acid, enanthic acid, pelargonic acid, capric acid, undecylenic acid, lauric acid, myristic acid, palmitic acid, oleic acid, stearic acid, linolenic acid, arachidonic acid, benzethonium chloride, benzethonium bromide, benzalkonium chloride, cetylpyridium chloride, edetate di sodium dihydrate, sodium desoxycholate, sodium deoxyglycolate, sodium glycocholate, sodium caprate, sodium taurocholate, sodium hydroxybenzoyal amino caprylate, dodecyl dimethyl aminopropionate, L-lysine, glycerol oleate, glyceryl monostearate, citric acid, peppermint oil and combinations thereof.

Surfactants suitable for use in the present application include, but are not limited to, sorbitan esters, docusate sodium, sodium lauryl sulphate, cetriride and combinations thereof.

Sweeteners suitable for use in the present application include, but are not limited to, aspartame, saccharine, potassium acesulfame, sodium saccharinate, neohesperidin dihydrochalcone, sucralose, sucrose, dextrose, mannitol, glycerin, xylitol and combinations thereof.

Sweetness enhancers suitable for use in the present technology include, but are not limited to, ammonium salt forms of crude and refined glycyrrhizic acid.

Flavoring agents suitable for use in the present technology include, but are not limited to, peppermint oil, menthol, spearmint oil, citrus oil, cinnamon oil, strawberry flavor, cherry flavor, raspberry flavor, orange oil, tutti frutti flavor and combinations thereof.

pH adjusting agents suitable for use in the present subject matter include, but are not limited to, hydrochloric acid, citric acid, fumaric acid, lactic acid, sodium hydroxide, sodium citrate, sodium bicarbonate, sodium carbonate, ammonium carbonate, sodium acetate and combinations thereof.

In another preferred embodiment, the pharmaceutical compositions of the present application do not contain a preservative.

Pharmaceutical compositions of the present technology may be formulated in any dosage form including but not limited to aerosol including metered, powder and spray, chewable bar, bead, capsule including coated, film coated, gel coated, liquid filled and coated pellets, cellular sheet, chewable gel, concentrate, elixir, emulsion, film including soluble, film for solution and film for suspension, gel including metered gel, globule, granule including granule for solution, granule for suspension, chewing gum, inhalant, injectable including foam, liposomal, emulsion, lipid complex, powder, lyophilized powder and liposomal suspension, liquid, lozenge, ointment, patch, electrically controlled patch, pellet, implantable pellet, pill, powder, powder, metered powder, solution, metered solution, solution concentrate, gel forming solution/solution drops, spray, metered spray, suspension, suspension, syrup, tablet, chewable tablet, coated tablet, coated particles in a tablet, film coated tablet, tablet for solution, tablet for suspension, orally disintegrating tablet, soluble tablet, sugar coated tablet, dispersible tablet, tablet with sensor, tape, troche and wafer and extended release and delayed release forms thereof.

In a preferred embodiment, the pharmaceutical compositions of the present technology are in tablet form. In a more preferred embodiment, the pharmaceutical compositions of the present subject matter are in a dispersible tablet form. In an even more preferred embodiment, the pharmaceutical compositions of the present subject matter are in a water-dispersible tablet form. In a most preferred embodiment, the pharmaceutical compositions of the present technology are in a water-dispersible tablet form wherein the tablet is scored such that the tablet is dividable into four equal parts.

In a preferred embodiment, when the pharmaceutical compositions of the present application are in a water-dispersible tablet form the tablet dispersion time is about 70 seconds or less, more preferably about 60 seconds or less and even more preferably about 40 seconds or less, even more preferably about 30 seconds or less, even more preferably about 20 seconds or less, even more preferably about 10 seconds or less and even more preferably about 5 seconds or less.

As used herein the term "pharmaceutically acceptable" refers to ingredients that are not biologically or otherwise undesirable in an oral application.

As used herein, all numerical values relating to amounts, weights, and the like, are defined as "about" each particular value, that is, plus or minus 10%. For example, the phrase "10% w/w" is to be understood as "9% to 11% w/w." Therefore, amounts within 10% of the claimed value are encompassed by the scope of the claims.

As used herein "% w/w" refers to the weight percent by weight of the total formulation.

As used herein "% w/v" refers to the weight percent by volume of the total formulation.

As used herein the term "effective amount" refers to the amount necessary to treat a subject in need thereof.

As used herein the term "treatment" or "treating" refers to alleviating or ameliorating ARDS or symptoms of ARDS.

As used herein, the term "stable" includes, but is not limited to, physical and chemical stability.

Pharmaceutically acceptable salts of that can be used in accordance with the current application include but are not limited to hydrochloride, dihydrate hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, mesylate, maleate, gentisinate, fumarate, tannate, sulphate, tosylate, esylate, gluconate, glucoronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

Throughout the application, the singular forms "a," "an," and "the" include plural reference unless the context clearly dictates otherwise.

The disclosed embodiments are simply exemplary embodiments of the inventive concepts disclosed herein and should not be considered as limiting, unless the claims expressly state otherwise.

The following examples are intended to illustrate the present technology and to teach one of ordinary skill in the art how to use the formulations of the instant subject matter. They are not intended to be limiting in any way.

EXAMPLES

Example 1—Administration of 2.5 mg/kg/day DITPA to a Pediatric Subject (Prophetic)

Method 3,5-diiodothyropropionic acid ("DITPA") was administered to a pediatric patient suffering from Allan-Herndon-Dudley Syndrome at a daily dosage of 2.5 mg/kg/day divided over three administration spaced 8 hours apart for 2 weeks. 28 days following initial administration T3 serum levels, T3 brain levels, T4 serum levels and TSH serum levels were assessed.

Results

The pediatric patient's T3 serum levels would be reduced to a normal level, T3 brain levels would be increased to a normal level, T4 serum levels would be maintained at or increased to a normal level and TSH serum levels would be maintained at or decreased to a normal level.

Example 2—Dosing Regimen for a Pediatric Subject (Prophetic)

Method 3,5-diiodothyropropionic acid ("DITPA") was administered to a pediatric patient suffering from Allan-Herndon-Dudley Syndrome at a daily dosage of 1 mg/kg/day divided over three administration spaced 8 hours apart for 2 weeks. Following the first 2 weeks, the daily dosage was increased to 2 mg/kg/day for 2 additional weeks. Following the 2 additional weeks, T3 serum levels were assessed. The patient was found to have T3 serum levels more than 15% below normal. The patient was then administered DITPA at a daily dosage of 1.5 mg/kg/day for 28 days at which time T3 serum levels were reassessed. Upon reassessment T3 serum levels were normal.

Results

The dosing regimen would successfully identify proper dosing for the pediatric patient to maintain normal T3 serum levels.

Example 3—Dosing Regimen for a Pediatric Subject (Prophetic)

Method

DITPA was administered to a pediatric patient suffering from Allan-Herndon-Dudley Syndrome at a daily dosage of 1 mg/kg/day divided over three administration spaced 8 hours apart for 2 weeks. Following the first 2 weeks, the daily dosage was increased to 2 mg/kg/day for 2 additional weeks. Following the 2 additional weeks, T3 serum levels were assessed. The patient was found to have T3 serum levels more than 15% above normal. The patient was then administered DITPA at a daily dosage of 2.5 mg/kg/day for 28 days at which time T3 serum levels were reassessed. Upon reassessment T3 serum levels were normal.

Results

The dosing regimen would allow successful identification of proper dosing for the pediatric patient to maintain normal T3 serum levels.

Example 4—Dosing Regimen for a Pediatric Subject (Prophetic)

Method

DITPA was administered to a pediatric patient suffering from Allan-Herndon-Dudley Syndrome at a daily dosage of 1 mg/kg/day divided over three administration spaced 8 hours apart for 2 weeks. Following the first 2 weeks, the daily dosage was increased to 2 mg/kg/day for 2 additional weeks. Following the 2 additional weeks, T3 serum levels were assessed. The patient was found to have T3 serum levels more than 15% below normal. The patient was then administered DITPA at a daily dosage of 1.5 mg/kg/day for 28 days at which time T3 serum levels were reassessed. Upon reassessment T3 serum levels were again found to be more than 15% below normal. The patient was then administered DITPA at a daily dosage of 1.0 mg/kg/day for 28 days at which time T3 serum levels were reassessed. Upon reassessment T3 serum levels were found to be normal.

Results

The dosing regimen would enable successful identification of proper dosing for the pediatric patient to maintain normal T3 serum levels.

Example 5—Detailed Case Reports

Family #8 (Subjects A1 and A2)

The affected monozygotic twin boys, hereafter referred to as subject A1 and A2, were born in Israel, to Ashkenazi, non-consanguineous parents living in Australia. The mother, carrier of Gaucher disease, had gestational diabetes mellitus which was managed with diet. Amniocentesis revealed normal male karyotype. Born at 36-37 weeks gestation, weights of twins 1 and 2 respectively were 2490 and 2733 gm (10th to 25th centile). Apgar scores were 9 and 9 for both twins. Delay in ability to make eye contact until 3 months and to smile until 4 months brought the twins to medical attention. At age 5 months both were admitted for bronchiolitis. The twins were referred to a Child Developmental Center and found to have gross and fine motor delay. By the age of 10 months, they could roll over but not sit unsupported. More specifically, they had a prominent axial hypotonia with poor head control and lag. They also had dystonic posture with hands fisted and held in extreme supine position, and hyperextension of the legs. Deep tendon reflexes were hyperactive with extensor plantar response, but no clonus. The twins had broad foreheads, wide nasal bridge, high arched palate, dolichocephaly (circumferences on the $10^{th}$ centile), and some bitemporal hollowing.

Chemistry was normal except for high lactic acid, ammonia and creatine kinase. Blood and urine amino acids, uric acid, pyruvic acid acyl carnitine, acyl glycine and urine guanidinoacetate were normal. TSH was 4.7 and 4.1 mU/L (normal range 0.35-5.5). Examination of twin 2 cerebrospinal fluid for neurotransmitter disorders gave a negative result. Electroencephalograms (EEG), awake and asleep, were normal. At 9 months both twins showed delayed myelination on magnetic resonance imaging (MM) and a large choline peak on magnetic resonance spectroscopy (MRS) (1).

At 18 months of age, we found that in twin 1 and 2, respectively, serum T3 was 54 and 60% above the upper limit of normal (ULN), T4 was 26 and 20% below the lower limit of normal (LLN) and rT3 was 44 and 37% below the LLN with normal TSH of 4.0 and 3.7 mU/L. We also identified a mutation in the MCT8 gene; a single nucleotide substitution (c.962 C>T) producing a missense mutation (P321L) located in the 5th transmembrane domain of the molecule. The mother is heterozygous for the mutation and has a normal brother.

Their postnatal growth was similar to other subjects with MCT8 deficiency. While length progressed between the 10th to 25th centile, by the age of 6 months their weight dropped below the 1st centile. Treatment with DITPA was started at 25 months of age in both twins.

Family #10 (Subject B)

The affected boy, hereafter referred to as subject B, was born at term to non-consanguineous white European (Swiss) parents. His birth weight and length were 2840 g and 47.5 cm and Apgar score 9/9/10. Neonatal screen TSH was <15 mU/L (the cut off value for the program). Hypotonia was noted at 1 month of age and thyroid tests at 4 months showed a FT4 15% below the LLN for age and total T3 63% above the ULN. The MCT8 gene, sequenced in Dr. Theo Visser's laboratory, showed a single nucleotide substitution (c.733 C>T) producing a stop codon (R245X). The mother was heterozygous for the same mutation; a maternal uncle, now aged 22 years, does not walk or talk and has seizures. MM obtained at the ages of 3, 8 and 13 months showed various degrees of retarded myelination of the white matter, especially bifrontally. There was an increased myoinositol peak on MRS. Currently, at age 45 months, he cannot talk or walk but has no dyskinesia or seizures. Treatment with DITPA was started at 8.5 months of age.

Family #11 (Subject C)

The affected boy, hereafter referred to as subject C, was born in Canada to non-consanguineous Iranian parents. Born at 40 weeks of gestation, his birth weight and length were 3875 g and 50 cm. Neonatal screen TSH was <17 mU/L (the cut off value for the program). At 3 months of age, long crying spells and poor sleep were attributed to colic and the infant was treated with Ranitidine. By 4 months of age his grandmother noted poor head control and by 5 months hypotonia was obvious. This initiated a number of analyses, including blood and urinary amino acids and blood quantitative acylcarnitines which showed no gross abnormalities. Karyotype was normal. At 5 months MRI of the brain showed delayed myelination. This was still present, though at a lesser degree at 17 months of age. Muscle biopsy showed a decrease in cytochrome oxidase and an increase in citrate synthase. He was 18 months old when thyroid tests were obtained showing a FT4 40% below the LLN and a FT3 60% above the ULL. It is at this point that genetic diagnosis was sought. We identified a single nucleotide substitution (c.1238 C>T) in the MCT8 gene, producing a stop codon (Q380X). This is a de-novo mutation as it was not found in the mother. The child was growing normally between the 50th and 75th centile for length and between the 10th and 25th centile for weight. Dyskinetic episodes were noted only during febrile illnesses. At 21 months basal metabolic rate was +79%. Treatment with DITPA was started at 25 months of age.

It is to be understood that the methods of treating AHDS by administering DITPA are not limited to the specific embodiments described above but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of treating Allan-Herndon-Dudley syndrome, the method comprising administration of 3,5-diiodothyropropionic acid (DITPA) to a subject in need thereof, wherein administration begins within three days after birth of the subject, and the administration is in a total daily dosage of at least 2 milligrams per kilogram of body weight of the subject, and, wherein the administration reduces triiodothyronine (T3) serum levels to normal, increases T3 brain levels to normal, increases to, or maintains, normal serum levels of thyroxine (T4), and decreases to, or maintains, normal thyroid stimulating hormone (TSH) serum levels.

2. The method of claim 1, wherein the total daily dosage of DITPA is divided in two parts and each part is administered every 12 hours or twice a day.

3. The method of claim 1, wherein the total daily dosage of DITPA is divided into three parts and each part is administered every 8 hours or three times a day.

4. The method of claim 1, further comprising the following steps:
   a) administering 3,5-diiodothyropropionic acid (DITPA) daily at a first daily dosage for two weeks to a subject in need thereof;
   b) administering DITPA daily at a second daily dosage for two weeks to the subject, wherein the second daily dosage is equal to or greater than the first daily dosage; and
   c) measuring triiodothyronine (T3) serum levels in the subject, wherein if T3 serum levels are normal the second daily dosage is continued to be administered daily.

5. The method of claim 4, further comprising the following steps:
   d) adjusting the daily dosage of DITPA administered to the subject based on T3 serum levels of the subject measured in step c),
   wherein if the T3 serum levels are too high a third daily dosage is administered, wherein the third daily dosage in greater than the second daily dosage,
   and wherein if the T3 serum levels are too low a fourth daily dosage is administered daily, wherein the fourth daily dosage is less than the second daily dosage; and
   e) measuring T3 serum levels of the subject about 28 days following initial administration of the third daily dosage or the fourth daily dosage,
   wherein if T3 serum levels are normal the third daily dosage or the fourth daily dosage is continued to be administered daily.

6. The method of claim 5, further comprising the following steps:
   f) adjusting the daily dosage of DITPA administered to the subject based on T3 serum levels of the subject measured in step e),
   wherein if the T3 serum levels are too low following daily administration of the third daily dosage then the subject is administered the second daily dosage,
   and wherein if the T3 serum levels are too low following daily administration of the fourth daily dosage then the subject is administered the first daily dosage and wherein if the T3 serum levels are too high following daily administration of the fourth daily dosage then the subject is continued to be administered the second daily dosage.

7. The method of claim 5, wherein the third daily dosage is about 2.5 milligram per kilogram of body weight of the subject.

8. The method of claim 5, wherein the fourth daily dosage is about 2 milligram per kilogram of body weight of the subject.

9. The method of claim 4, wherein the second daily dosage is about 2 milligram per kilogram of body weight of the subject.

10. The method of claim 4, wherein each daily dosage of DITPA is administered to a subject in need thereof at one time, once a day.

11. The method of claim 4, wherein the daily dosage of DITPA is divided in two parts and each part is administered about every 12 hours or twice a day.

12. The method of claim 4, wherein the daily dosage of DITPA is divided into three parts and each part is administered about every 8 hours or three times a day.

13. A method of treating Allan-Herndon-Dudley syndrome comprising the following steps:
   a) administering 3,5-diiodothyropropionic acid (DITPA) daily at a first daily dosage, of at least 2 milligrams per kilogram of body weight of a subject, for two weeks to the subject in need thereof; and
   b) administering DITPA daily at a second daily dosage for two weeks to the subject, wherein the second dosage is greater than the first daily dosage,
wherein daily administration in step a) begins within three days following birth of the subject.

14. The method of claim 13, wherein the first daily dosage is about 2 milligram per kilogram of body weight of the subject.

15. The method of claim 13, wherein the second daily dosage is about 2.5 milligram per kilogram of body weight of the subject.

* * * * *